United States Patent [19]

Petigara et al.

[11] Patent Number: 5,008,395
[45] Date of Patent: Apr. 16, 1991

[54] PURIFICATION OF ISOTHIAZOLONES

[75] Inventors: Ramesh B. Petigara, Hatfield; Douglas N. Sharp, Bensalem, both of Pa.

[73] Assignee: Rohm and Haas Company, Philadelphia, Pa.

[21] Appl. No.: 289,069

[22] Filed: Dec. 22, 1988

[51] Int. Cl.$^5$ ............................................. C07D 513/00
[52] U.S. Cl. .................................................... 548/213
[58] Field of Search ........................................ 548/213

[56] References Cited

U.S. PATENT DOCUMENTS

| 3,118,901 | 1/1964 | Hatchard et al. | 260/302 |
| 3,761,488 | 9/1978 | Lewis et al. | 548/513 |
| 4,053,479 | 10/1977 | Miller et al. | |
| 4,262,127 | 4/1981 | Virgilio et al. | 548/213 |

FOREIGN PATENT DOCUMENTS 95907 4/1988 European Pat. Off. .
271761 6/1988 European Pat. Off. .

OTHER PUBLICATIONS

Cheronis N. D. "Semimicro Experimental . . ." Brooklyn College, 1958.

*Primary Examiner*—Nicholas S. Rizzo
*Assistant Examiner*—Celia Chang
*Attorney, Agent, or Firm*—Michael B. Fein

[57] ABSTRACT

A process for obtaining pure 2-substituted-3(2H)-isothiazolones is presented, wherein the substituent is alkyl, linear or branched. By developing suitable conditions, the isothiazolone hydrochloride is isolated from the complex reaction media wherein it is formed as readily filterable crystals of high purity. Such purified crystals are then utilized in isolation of isothiazolone of high purity.

16 Claims, No Drawings

PURIFICATION OF ISOTHIAZOLONES

BACKGROUND OF THE INVENTION

This invention relates to the purification of complex reaction mixtures to obtain high purity (>98%) isothiazolones by first forming and isolating readily filterable high purity crystalline salts of the isothiazolones of the formula:

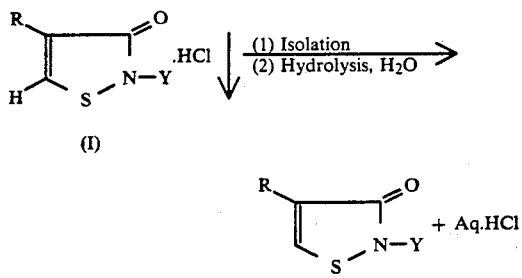

wherein R is hydrogen or methyl and Y is a linear or branched alkyl of from 3 to 10 carbon atoms, followed by hydrolysis with water to the desired isothiazolones which are well known biocides.

A process for preparing isothiazolone reaction mixtures is described in U.S. Pat. No. 3,761,488, where a N,N'-disubstituted 3,3'-dithiodipropionamide is halogenated and cyclized with such reactants as chlorine or sulfuryl chloride to a crude reaction mixture containing 2-substituted-3-isothiazolone hydrohalide salt in solution. The halogenation reactant is maintained at about 3 equivalents of halogen per equivalent of dithiodiamide to obtain a complete reaction which unfortunately contains small to significant amount of unwanted products such as 5-halo-2-substituted isothiazolone, 4-halo-2-substituted isothiazolone, 4,5-dihalo-2-substituted isothiazolone, 3-halo-N-substituted alkyl propionamide, and other amide impurities. From the reaction mixture the hydrohalide salt is crystallized, isolated and then hydrolyzed with water to the desired isothiazolone of high purity (>98%).

An alternate route to isothiazolones is disclosed in European Patent 95,907, wherein a 3-mercaptopropionamide is treated with at least about 2 equivalents of chlorine or other halogenating agent to form and isolate the isothiazolone hydrohalide salt, followed by its hydrolysis to obtain the desired isothiazolone.

Both of the above processes are also useful in preparing the 4-methyl-2-substituted isothiazolones from the corresponding mercaptoisobutyramide or dithiodiisobutyramide intermediate.

However, in these processes some amounts of above mentioned impurities are formed. For improvement of product quality, safety reasons, and for many end uses, it is desirable to remove such impurities.

The materials to be chlorinated and cyclized to the corresponding isothiazolone hydrochloride containing reaction mixture have the following formula:

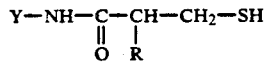

-continued
and

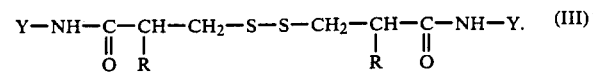

Some solvents used to conduct the chlorination/cyclization has been a lower alkyl ester, such as ethyl acetate, butyl acetate, and the like. Upon removal of the excess hydrogen chloride, the isothiazolone salt precipitates. There are disadvantages to using such solvents because:

a. certain impurities precipitate with the desired product and be removed only with difficulty;

b. the solvent gets hydrolyzed during the hydrolysis of the isothiazolone salt, leading to a loss of solvent on recovery or introduction of the hydrolyzed solvent as an impurity in the desired product;

c. upon recycle the solvent or its hydrolysed products react during the chlorination/cyclization step to lower product yield and have deleteriously affect; or d. the desired hydrochloride salt may be more soluble in the ester solvent to cause significant yield losses.

It is an object of this invention to provide a suitable solvent for the chlorination reaction and subsequent isothiazolone purification which is inert to chlorination under the reaction conditions, inert to the hydrolysis reaction conditions employed to hydrolyse the salt, sufficiently volatile to be removed completely from the isothiazolone when desired, and possessing such solubility characteristics for the isothiazolone salt allowing quantitative separation of pure salt after removal of excess hydrogen chloride. It is a further object to provide processing conditions for the crystallization which produce pure clustered crystal aggregates of a size and shape suitable for ease of filtration and washing, and which avoid forming secondary nucleation tiny crystals which clog filtration apparatus and are difficult to free from mother liquor containing reaction impurities.

European Patent 95,907 teaches other solvents may be used, such as toluene or perchloroethylene. These solvents are reactive under halogenation conditions or are toxic or create environmental problems.

European Patent Application 271,761, teaches purification of crude isothiazolones, by isolation of the isothiazolone (not the hydrochloride) and process impurities (in an unspecified procedure), dissolving this material in an organic solvent immiscible with water, treating this solution with a strong acid, such as hydrogen chloride, to form the salt, followed by separation and hydrolysis of the salt in the presence of the organic solvent. Monochlorobenzene and chlorinated hydrocarbons are mentioned as solvents, but are not used. There is no teaching in this reference which would lead one to the present invention.

DESCRIPTION OF THE INVENTION AND ITS PREFERRED EMBODIMENTS

This invention is a process for preparing substantially pure (over 98%) isothiazolone by preparing crystalline isothiazolones monohydrochloride salts of the formula:

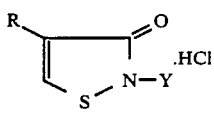

wherein R is hydrogen or methyl and Y is linear or branched alkyl group of from 3 to 10 carbon atoms, by the chlorination of compounds of the formula:

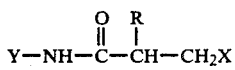

wherein X is —SH or

wherein the improvement comprises:

(a) conducting the chlorination in a chlorinated hydrocarbon solvent to afford a crude reaction mixture containing isothiazolone hydrochloride and excess hydrogen chloride in solution;

(b) reducing the excess hydrogen chloride to below about 120% of that needed to form the salt;

(c) forming a seeded solution;

(d) cooling the seeded solution under temperature/time conditions to form readily filterable pure crystals of the salt; and (e) collecting the pure crystals.

It is desired to employ a solvent which is essentially unreactive with chlorine during the chlorination/cyclization reaction and is further essentially unreactive with water during the conversion of the isothiazolone hydrochloride to the free isothiazolone. Appropriate solvents are chlorinated hydrocarbons, either aromatic or aliphatic such as monochlorobenzene, chlorotoluene, dichlorobenzene, ethylene dichloride or perchloro ethylene and the like. The preferred solvent is monochlorobenzene. An appropriate solvent is selected based on least toxicity, moderate volatility, low cost, least environmental problems, etc.

The use of monochlorobenzene, however, had a serious deficiency because the reaction mixture on degassing gave the isothiazolone hydrochloride in the form of thin, long needles forming a paste which is impossible to collect. Monochlorobenzene is trapped within the fine crystals, and any impurities dissolved in the monochlorobenzene are difficult to remove. This deficiency is also noted with other chlorinated solvents, such as perchloroethylene.

Thus, to be able to utilize the chlorinated hydrocarbons as a solvent in the chlorination and as a crystallizing media for the isothiazolone salt, it was necessary to discover a means for drastically altering the crystal size and shape, so as to produce easily filterable high purity large crystals.

We have found that the isothiazolone hydrochloride salt is much more soluble in the reaction mixture containing an excess of hydrogen chloride generated during the chlorination in the chlorinated hydrocarbons than it is in monochlorobenzene containing little or no hydrogen chloride. Stated another way, the solubility of the monohydrochloride salts of the 2-substituted isothiazolones of this invention is significantly decreased as the concentration of hydrogen chloride in the reaction mixture decreases. Elimination of the large excess of hydrogen chloride from the chlorination mixture allows a method for forming a seeded solution of the isothiazolone hydrochloride salt either in the mixture, or creating conditions where separately added seed crystals of the salt will neither redissolve nor cause further massive precipitation of small crystals due to secondary nucleation.

In the initial step of the present process, the appropriate compound of formula II or III is reacted with chlorine in the presence of the chlorinated hydrocarbon solvent. Even under the controlled chlorination conditions small to appreciable amounts of 4-chloro-, 5-chloro-; 4,5-dichloroisothiazolones and other by-products are formed.

Other impurities which may be present in the reaction mixture include unreacted compound III and 3-chloro-N-(alkyl or cycloalkyl)propionamide (or isobutyramide). Formation of such by-products detracts from the yield of non-chlorinated isothiazolone salt, and such impurities will remain in the solvent mixture.

The stoichiometry requires that 2 moles of chlorine react with compound II to form the salt and 3 excess moles of hydrogen chloride, and that 3 moles of chlorine react with compound III to form the salt and 5 excess moles of hydrogen chloride. Thus the solvent for the formed isothiazolone is a mixture of appropriate inert solvent, such as chlorobenzene, with excess hydrogen chloride and various impurities as are mentioned generated in the reaction. In such a mixture, the desired isothiazolone salt is fully soluble.

The removal of the excess hydrogen chloride that is degassing should be carried out without introducing any new chemicals. Thus, it is best removed by an appropriate physical process, such as evaporation. Preferred methods are sparging of the mixture with an appropriate inert gas, such as nitrogen, which will not further react with the isothiazolone or hydrogen chloride, or by applying sufficient vacuum to cause the hydrogen chloride and some solvent to volatilize. The degassing may be carried out over a range of temperatures; preferred is a temperature in the range of from about 46° to about 60° c. and most preferred is from about 46° to 52° C.

A combination of sparge and vacuum may also be employed. The excess hydrogen chloride removed from the reaction mixture may be neutralized with base or collected in other ways to avoid corrosion or contamination. Some solvent also gets removed at this point. If necessary additional solvent may be added to the reaction mixture to maintain a particular solids level.

The level of remaining hydrogen chloride is measured by titration. The level, which prior to the sparging, vacuum, or other reduction operation was about 220% of that needed to form the salt, should now be below about 120% of that needed to form the salt; expressed in another way, the reaction system should contain less than 0.2 mole of hydrogen chloride beyond that present in 1 mol of the isothiazolone monohydrochloride salt.

At this point, with the temperature preferably high enough to maintain most if not all of the salt in solution, and with the concentration of the salt near the concentration at which crystallization could occur, seed crystals are formed or added. If added from an external source, such seed crystals are preferably small, such as below about 100 microns by 30 microns by 30 microns, and may contain entrapped solvent. The amount of added seed crystals is preferably from about 3 to about 6 weight percent of of the batch, although somewhat smaller or larger amounts may be used.

It is preferred to form the seed crystals internally in the degassed reaction mixture by control of temperature and extent of removal of hydrogen chloride. The initial crystals formed are small, such as about 100 microns by 30 microns by 30 microns or smaller, and will consist of from about 25 to about 60% of the total salt in the partially precipitated mixture. Preferred is from about 25 to about 35% present as seed crystals; this level may be achieved by dissolving some of the initially precipitated small crystals by upward temperature adjustment.

It is common knowledge in crystallization that creation of or introduction of seed crystals can lead to rapid crystallization of the whole mass of dissolved crystallizable material. In the present case, the rapid crystalization is eliminated by careful control of temperature, optionally including a step where the temperature is raised slightly or cycled to adjust the size and amount of seed crystal present. Then the initial seed crystals are allowed to "ripen", i.e., grow slightly larger, but without significant crystallization of new material from the dissolved phase. The "ripening" phase produces modified seed crystals which are more useful in controlling the subsequent crystallization.

Once appropriate "ripened" seed crystals are available, crystallization to form the filterable large clustered crystals is best conducted by cooling of the reaction medium. The temperature should be lowered at a slow rate, preferably about 1 degree C. or less/ 5 minutes. Also preferred is to cool the batch, initially temperatures of from about 45° to about 55° c., preferably about 52° to about 53° c., through the first 10-degree to 15-degree drop (to about 30 to about 45, preferably to about 42° to about 43°) at a slower rate than for subsequent cooling; a rate of about 1° c./ 15 minutes has been found most effective. Further cooling to room temperature and below may be effected at a somewhat faster rate, but in no case above about 1° / 5 minutes. Intermediate rates may also be employed during the mid-portion of the cooling cycle. The cooling rate selected is such that it avoids any significant supersaturation which may lead to massive secondary nucleation passing tiny new crystals. A final temperature of room temperature or below, preferably about 20°, is utilized.

The clustered crystals formed by the present process may be collected by conventional means, including vacuum draining, mechanically pressing the filter cake, use of a pressure column, and the like. The crystals may be washed with monochlorobenzene to remove residual mother liquor containing soluble impurities; if desired, other appropriate chlorinated solvents which will dissolve the impurities may be used in the wash step.

The isothiazolone salt is converted to the free isothiazolone by hydrolysis with water by conventional known means, the water phase containing HCl is separated, the organic phase containing product is preferably re-washed with water, the water phase again separated. From the product layer the residual monochlorobenzene or other appropriate solvent is removed by application of vacuum and distillation or stripping, such as steam stripping.

As noted earlier, the present process is mainly useful for the purification of isothiazolones wherein the 2-substituent radical is an alkyl group, linear or branched, of from three to ten carbon atoms. When the alkyl group is less than three carbon atoms, the solubility of the isothiazolone salt is so small in the organic phase that the present process is not effective. If the substituent group is higher in molecular weight than those shown here, the solubility of the hydrochloride salt will be lessened in monochlorobenzene to the extent that the present process cannot be effectively practiced. Within the present series of isothiazolones, some experimentation may be necessary, such as adjustment of solids, extent of removal of excess hydrogen chloride, and adjustment of temperature, to produce the best results in terms of extent of aggregated crystals and yields of recovered product.

The preferred isothiazolones or isothiazolone hydrochloride salts for purification by the process of the present invention are those where R is H and Y is C3–C10 alkyl. Especially preferred is n-octylisothiazolone, wherein R is H and Y is n-octyl.

The process is not suitable for isothiazolones substituted with chlorine in the four and/or five position, as the hydrochloride salts are too soluble in the appropriate solvents. The process is less suitable for purification of hydrohalide salts other than the hydrochloride, mainly for economic reasons.

The purification process described herein may also be applied to purification of isothiazolones made by other processes, such as by processes taught by Virgilio et al. in U.S. Pat. Nos. 4,281,136 and 4,508,136, wherein 2-alkyl-3-haloisothiazolium salts may be converted to a mixture of the corresponding isothiazolone with by-products related to the salts.

The isothiazolones are known to have many preservative uses including deodorizers, preservative for liquid and powder soaps, food processing, dairy chemicals, food preservatives, animal food preservatives, preservatives for wood, lazures and paints, preservatives for paint films and plastics, hospital and medical antiseptics, metal working fluids, cooling water, air washers, paper treatment, petroleum products, adhesives, pigment slurries, latexes, leather and hide treatment, agricultural formulations, mining, nonwoven fabrics, petroleum storage, rubber, sugar processing, tobacco, cosmetics, chemical toilets, household laundry, detergent, and dishwashing products, diesel fuel additives, waxes and polishes and many other applications where water and organic materials come in contact under conditions which allow the growth of undesired microorganisms.

Isothiazolones also are used as disinfectants, in oil field water treatment, as watercooling system microbiocides, as preservatives for aqueous dispersions or organic polymers, as wood pulp white water slimicides, as cosmetic preservatives, as cutting oil, et fuel, and heating oil preservatives, and the like. They are also useful in adhesives, agricultural chemical preservation, air washing devices, alcohol stabilization, carpet backing, caulks and sealants, ceramics, cleaners, cement modifiers, diesel and other fuels, electrocoating systems, electronic circuitry, commercial enzymes, fabric softeners, feed preservation, fibers, printing, household and industrial cleaners, inks, laundered goods, laundry wash water, marine antifoulants, such as ship bottoms, propellors, fishnets, and the like, medical devices, membranes, odor control, pasteurization baths, photographic emulsions, pharmaceutical and therapeutic uses, preservation of reagent chemicals, sanitizers, swimming pools, textile manufacture and uses, toiletries, waste treatment, water purification, and the like.

Solutions of isothiazolones are also applied to a solid substrate, such as fabric, leather, or wood, as a preservative, or admixed with plastics.

The present materials, having organic solubility and limited water solubility have especial utility in preservatives for starch and dextrin pastes used on wallpaper, as preservatives for plastics, such as plasticized poly(vinyl chloride), and as mildewcides for painted surfaces where the paint is applied as a water-based latex.

The isothiazolones prepared by the process of the present invention may also be useful in the various applications mentioned herein when combined with other isothiazolones, such as 5-chloro-2-methylisothiazolone,2-methylisothiazolone, and mixtures thereof. The present isothiazolones may also be useful in combination with other biocides.

The present invention is especially useful in the preparation of 2-n-octylisothiazolone which offers superior resistance to mildew growth, especially on latex paints, but is also effective in solvent based paints. Mildew in paints is noted as disfigurement of exterior house paints and other coatings by a superficial fungal dark-colored growth caused mainly by Aureobasidium pullulans, cladosporium, and alertaria pullulans. The n-octylisothiazolone is effective in killing the organism and so preventing discoloration and in killing bacteria responsible for paint spoilage during storage.

The examples are intended to illustrate the present invention and not to limit it except as it is limited by the claims. All percentages are by weight unless otherwise specified.

EXAMPLE 1 - 2-n-Octylisothiazolone, hydrochloride salt

This example illustrates the formation of clustered readily filterable crystals of high purity hydrochloride salt of 2-n-octyl isothiazolone by controlled removal of excess hydrogen chloride, generation of seed crystals, temperature cycling of seed crystals, and controlled cooling of the seeded mixture.

In a 1325 l. reactor equipped with an agitator, means for adding liquids, means for adding gases, means for pumping liquid from the reaction and recirculating it to the reactor, and a vent equipped for applying vacuum and for scrubbing or collecting removed volatiles, is added 273.4 kgs. of monochlorobenzene. Over a period of four hours fed 729 kgs. of 55% noctyl-3-mercaptopropionamide in monochlorobenzene and 195.9 kgs. of chlorine gas, while agitating and maintaining the temperature at 46°. The chlorine feed was then continued to add 63.8 kgs. over a further two hours. The batch is analyzed as follows:

| | |
|---|---|
| 2-n-Octylisothiazolone (OIT) | 29% |
| Hydrogen chloride bound to OIT | 5.5% |
| Hydrogen chloride free in solution | 6.5% |
| Monochlorobenzene | 52% |
| Process impurities | 7% |

Analysis is by gas chromatographic analysis of the organic layer after weighing an aliquot, treatment of the solution with water/ethyl acetate, and analysis of a known weight of the ethyl acetate solution. The process impurities include 4-chloro-2-octylisothiazolone, 4,5-dichloro-2-octylisothiazolone 3-chloro-N-octylpropionamide and related amide by-products. The hydrogen chloride content of the reaction mixture is measured by titration of an aliquot of known weight with 0.1 N sodium hydroxide to a phenolphthalein endpoint. The amount bound as the monohydrochloride was calculated based on OIT concentration.

While maintaining agitation and temperature control to 46° C. the reaction is sparged with nitrogen (feed rate 566.4 liters/minute at standard conditions) for 8 hours. After about 4 hours, small crystals of the 2-octyl-3(2H)isothiazolone hydrochloride began to precipitate; at the end of the degassing, the batch contained about 22% weight percent of precipitated solids consisting of the monohydrochloride salt. The batch was again analyzed:

2-n-Octylisothiazolone (OIT).........35.5
Hydrogen chloride bound to OIT........6.5
Hydrogen chloride free in solution..<0.5
Monochlorobenzene......................49
Process impurities....................8.5

Three separate repeats of this process afforded values of 21.8% solids precipitated as monohydrochloride salt from the batch and 107.5 % of HCl present relative to the stoichiometric amount needed to form the monohydrochloride salt.

The batch is cooled to 38° c., then re-heated to 46° c. The cycle is repeated two to three times, with agitation maintained throughout. The heating and cooling rates were both 1°/5 minutes. The batch is then cooled to 20° c. at the same rate, to give clustered crystals representing 36 weight percent of the batch. The crystallized batch is readily filtered on a pressure column filter at 1400-2100 gms/sq.cm. nitrogen pressure. The wet filter cake of crystals was then washed with 455 kgs. of monochlorobenzene at 20° c. An aliquot of the snow-white crystals is dried in a vacuum oven (45° c./10 mm. mercury) for one hour, and is analyzed as OIT 85.3%; HCl 14.5%; total accountability 99.8%.

EXAMPLE 2 - Comparative Example

This example illustrates the formation of long thin needles like crystals which were extremely difficult to filter and to wash, and is presented here to show the difficulties of purification when utilizing an inert solvent without applying the critical steps of the present invention.

The process of Example 1 is followed until the chlorination step is completed. Vacuum (50-20 mm. mercury) is then applied to the reaction mixture with no control of reaction temperature. After four hours, the reaction is at room temperature, and long thin crystals of OIT.HCl (ca. 300×10×10 microns) precipitates as a paste soaking-up all of the solvent. When filtration of the paste was attempted, crystals free of solvent could not be isolated, either by use of a fritted glass dip stick or of a Buechner funnel under vacuum.

EXAMPLE 3 - 2-n-Octylisothiazolone, hydrochloride salt

This example illustrates the use of variable rate cooling to produce clustered crystals, readily filterable, and of high purity.

The steps of Example 1 are followed through the degassing step. The mixture containing small crystals (21% solids) is heated to 52° c. with agitation and allowed to equilibrate until the content of undissolved "seed" crystals is reduced to 12% of the batch weight. The mixture is then cooled from 52° c. to 42° c. at a rate of 1° c./15 minutes, from 42° c. to 32° c. at 1° c./10 minutes, and from 32° c. to 20° c. at a rate of 1~/5 minutes. The mixture is then held at 20° prior to filtration. Readily filterable crystals (size, 300×150×100 microns free of fines) of high purity are obtained after washing with MCB.

EXAMPLE 4 - 2-n-Octylisothiazolone

This example illustrates the conversion of the purified crystals of OIT hydrochloride to free OIT of high purity.

Wet-cake clustered crystals of OIT monohydrochloride (from Example 1) are directly treated in the pressure filtration column with an equal weight of hot (65° c.) water. After two hours of recirculation and one hour of separation, the upper aqueous layer is removed, and the organic layer further washed with an equal weight of water to remove any dissolved residual hydrochloric acid. The organic layer is then charged to a reactor equipped with an agitator, means for adding steam, means for applying vacuum, and means for adding and removing liquid, and stripped with steam at 80° c. under a vacuum of 50 mm. mercury to give 306 kgs. The final product, which analyzed as follows:

2-n-Octylisothiazolone (OIT)........98.5%
Hydrogen chloride ..................≦0.2%
Monochlorobenzene......................5%
Water................................0.2%
Process impurities..................≦0.1%

Crystals from the crystallization procedure of Example 3 gave equivalent results.

EXAMPLE 5 - 2-n-Octylisothiazolone

This example illustrates an alternate procedure for removal of solvent from the purified n-octylisothiazolone.

Crystals from Example 1 were charged to the reactor of Example 3, hydrolyzed as in Example 4, and stripped under vacuum to a final pressure of 10 mm. mercury at 55°. The purity and yield of OIT was equivalent to that from the stripping process of Example 4.

EXAMPLE 6 - Formulation of 2-n-Octylisothiazolone

This example illustrates a formulation. N-octylisothiazolone (320 kgs.) is dissolved in 1,2-propylene glycol (375 kgs.) to afford a 46% solution. The product may be added to a commercial acrylic latex paint formulation, preferably containing 0.012 kg./l. of zinc oxide, at a level of 0.0048 kgs. solution/l. of paint. The paint will exhibit good storage stability in the can against bacteriocidal attack, and will exhibit excellent resistance to mildew upon application to exterior surfaces.

N-octylthiazolone may also be dissolved at other concentrations in propylene glycol or other appropriate solvents to prepare solutions appropriate for use as mildewcides for fabric, hides or leather.

EXAMPLE 7 - n-Octylisothiazolone

This example illustrates preparation of pure OIT from the dithiodipropionamide starting material.

To a reactor as in Example 1 containing 110 kgs. of monochlorobenzene is co-fed (a) a slurry of 394 kgs. of N,N'-dioctyldithiodipropionamide in 483 kgs. of monochlorobenzene and (b) 145 kgs. of chlorine, the co-feed being carried out over a four hour period at 45° c. with agitation. An additional 49 kgs. of chlorine was further added over two hours. Further reaction steps are carried out as in Examples 3 and 4 to produce 301 kgs. of 99.5% pure OIT.

EXAMPLE 8

This example illustrates vacuum degassing to reduce and control the content of excess hydrogen chloride after chlorination is complete.

The reaction conditions of Example 1 are followed through the completion of chlorination. Vacuum is then applied with the temperature maintained at 46° and agitation of the mixture. The batch is then recirculated to aid in degassing and removal of excess hydrogen chloride under vaccuum. The pressure is lowered to 45 mm. mercury over a four hour period, at which point the OIT hydrochloride began to precipitate with a mild exotherm. The exotherm is controlled to maintain temperature at 46° c., and vacuum is continued without recirculation for another two hours. The crystals formed at this point could not be filtered readily because of their small size. The temperature is raised to 52° c. and held for one hour when the weight of precipitate crystals decreased from 21.6 to 12.8%. Hydrogen chloride present at this point was 112% of the stoichiometric amount needed for complete formation of the hydrochloride salt.

The batch is cooled to 20° c. with a variable cooling rate (as shown in Example 3) to afford readily filterable crystals. After hydrolysis and separation as in Example 4, the OIT was shown to be 98.8% purity with the remainder being essentially monochlorobenzene and water.

EXAMPLE 9

This example illustrates vacuum degassing at a temperature where the salt remains soluble.

The conditions of Example 1 are followed through the completion of the chlorination. The batch is then subjected to vacuum degassing at 60° and a final pressure of 75 to 80 mm. mercury. After four hours, the hydrogen chloride content is reduced to 108% of the stoichiometric amount. The mixture remains free of any solids. On cooling to 46° c., exothermic nucleation occurs. After equilibration for three hours at 46° C., the batch contained 19.6 wt.% solids precipitated as small unfilterable crystals. Upon following the temperature cycling and cooling process of Example 1, readily filterable crystals of dimensions 330×100×50 micron are formed. (After filtration and washing, the dimensions of the crystals are measured from calibrated photographs taken from optical microscopy). Hydrolysis and workup as in Example 4 affords the hydrochloride salt of OIT of high purity.

EXAMPLE 10

Use of variable cooling in precipitating clustered crystals after vacuum degassing of a solution.

The procedure of Example 9 is followed, except that after formation of the seed crystals, the temperature is raised to 52° c. and equilibrated for one hour to provide about 12 wt. % of the batch as seed crystals The cooling procedure of Example 3 is then employed to produce crystals of the salt which are readily filtered and washed.

EXAMPLE 11

This example illustrates vacuum degassing under conditions where smaller amounts of seed crystals were formed.

The procedure of Example 8 is followed, except that vacuum degassing is conducted at 52° c. at a final pressure of 50 mm. mercury, reached over a four-hour period, followed by at least a two-hour equilibration. Small crystals amounting to 10% of the total batch were formed. Cooling and isolation as in Example 3 affords crystals of the salt which are readily filtered and washed.

EXAMPLE 12

This example illustrates the preparation of filterable crystals through the external introduction of seed crystals. The process of Example 9 is followed to afford a clear solution at 60° c. containing 35.5 weight percent of isothiazolone and 6.6 weight percent hydrogen chloride. The batch is cooled to 52° c. at 1° c./5 minutes and 3 weight percent OIT.HCl crystals, size 150×30×30 microns are added. The batch is held at 52° c. for two hours, whereupon about 13 percent of the batch is present as small crystals. The process of Example 3 is then used to produce easily filterable crystals of high purity.

EXAMPLE 13 - n-Propylisothiazolone

A stirred slurry of 438 gms. of N,N'-di-n-propyl dithiodipropionamide in 660 gms. of monochlorobenzene is chlorinated at 46° c. with 320 gms. of chlorine over a three hour period. The reaction mixture is degassed under vacuum at 46° c., when small crystals of the 2-n-propylisothiazolone monohydrochloride precipitated. The reaction mixture is heated to 52° c. and then cooled to 20° c. under the variable rate cooling conditions of Example 3. The crystalline slurry is readily filtered on a Buechner funnel, washed with monochlorobenzene, and dried under vacuum to afford 464 gms. (86% yield) 99.5% of pure 2-n-propylisothiazolone hydrochloride.

EXAMPLE 14 - 2-n-Hexylisothiazolone

In a manner similar to that of Example 13, 377 gms. of a 40% solution of N,N'-di-n-hexyldithiodipropionamide in monochlorobenzene is reacted with 213 gms. of chlorine fed over three hours at a reaction temperature of 45° c. The reaction mixture is then degassed under vacuum at 46° c., when small crystals of the 2-n-hexylisothiazolone precipitated. The reaction mixture is heated to 52° c. and then cooled to 20° c. under the variable rate cooling conditions of Example 3. The crystalline slurry is readily filtered on a Buechner funnel, washed with 100 mls. of monochlorobenzene, and dried under vacuum to afford 355 gms. (80% yield) of 99% pure 2-n-hexylisothiazolone hydrochloride.

We claim:

1. In a crystallization process for preparing substantially pure isothiazolone by preparing crystalline isothiazolone monohydrochloride salts of the formula:

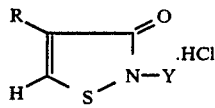

wherein R is hydrogen or methyl and Y is linear or branched alkyl, of from 3 to 10 carbon atoms, from a mixture derived by the chlorination of compounds of the formula

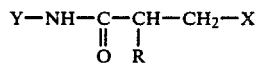

-continued where X is —SH or 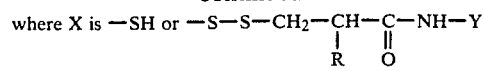

which comprises
conducting the chlorination in a chlorinated hydrocarbon solvent to afford a crude reaction mixture containing isothiazolone hydrochloride in a solution due to excess hydrogen chloride; the improvement comprising
(a) reducing the excess hydrogen chloride to about 1.2 moles per mol of isothiazolone while maintaining the temperature in a range of about 46° to 60° C.;
(b) cooling the reaction mixture slowly until tiny seed crystals form at about 46° C. then applying temperature/time thermal oscillating conditions to allow tiny seed crystals to grow in a timely manner into filterable crystals of the salt while avoiding formation of any new tiny crystals; and
(c) collecting the crystals 2. The process of claim 1 which further includes, subsequent to formation of the seeded solution, three or four cycles of heating and cooling the seeded solution at a temperature in the range of from about 46° C. to about 36° C. before finally cooling to 20° C.

3. The process of claim 1 wherein subsequent to formation of seeded solution the batch is heated to about 52° C. and then subjecting the solution to cooling at a variable rate, the rate near the beginning of the cooling being slowest and the rate near the middle being slower than the rate at the conclusion of the cooling.

4. The process of claim 1 wherein the solvent is monochlorobenzene.

5. The process of claim 2 wherein the solvent is ethylene dichloride or perchloro ethylene.

6. The process of claim 2 wherein Y is linear $C_3$ to $C_{10}$ alkyl and R is hydrogen.

7. The process of claim 6 wherein Y is n-propyl, n-hexyl or n-octyl.

8. The process of claim 7 wherein the size of the crystals are at least 200 microns by about at least 100 microns by about at least 50 microns.

9. Process of claim 1 further including hydrolyzing the filtered/washed crystals with water and isolating the isothiazolone having a purity over 95%.

10. The process of claim 9 wherein Y is n-octyl and R is hydrogen.

11. The process of claim 1 wherein the reducing of the excess hydrogen chloride is conducted at a temperature maintained at about 60° C. and then cooling to about 45°–46° C. until the solution equilibrates.

12. The process of claim 11 which further includes, subsequent to formation of the seeded solution, three or four cycles of heating and cooling the seeded solution at a temperature in the range of from about 46° C. to about 36° C. before finally cooling to 20° C.

13. The process of claim 11 wherein subsequent to formation of seeded solution the batch is heated to about 52° C. and then subjecting solution to cooling at a variable rate, the rate near the beginning of the cooling being slowest and the rate near the middle being slower than the rate at the conclusion of the cooling.

14. The process of claim 1 wherein the excess hydrogen chloride is reduced while maintaining the temperature at about 46° C.

15. The process of claim 14 which further includes, subsequent to formation of the seed solution, three or four cycles of heating and cooling the seeded solution at a temperature in the range of from about 46° C. to about 36° C. before finally cooling to 20° C.

16. The process of claim 14 wherein subsequent to formation of seeded solution the batch is heated to about 52° C. and then subjecting the solution to cooling at a variable rate, the rate near the beginning of the cooling being slowest and the rate near the middle being slower than the rate at the conclusion of the cooling.

* * * * *